United States Patent [19]

Block

[11] Patent Number: 4,834,067

[45] Date of Patent: May 30, 1989

[54] INSTRUMENT FOR INTERNAL HEMORRHOIDECTOMY

[76] Inventor: Irving R. Block, 3 Spruce Dr., East Patchogue, N.Y. 11772

[21] Appl. No.: 124,414

[22] Filed: Nov. 23, 1987

Related U.S. Application Data

[63] Continuation of Ser. No. 868,994, May 30, 1986, abandoned.

[51] Int. Cl.$^4$ ............................................. A61B 1/00
[52] U.S. Cl. ........................................................ 128/4
[58] Field of Search ...................................... 128/3, 4

[56] References Cited

U.S. PATENT DOCUMENTS

| | | | |
|---|---|---|---|
| 202,813 | 4/1878 | Hall | 128/4 |
| 295,798 | 3/1884 | Pagett | 128/4 |
| 312,123 | 2/1885 | Ives | 128/4 |
| 1,657,148 | 1/1928 | Catlin | 128/4 |
| 2,769,441 | 11/1956 | Abramson | 128/4 |
| 2,896,611 | 6/1959 | Moore | 128/3 |
| 3,976,054 | 8/1976 | Evans | 128/4 |

FOREIGN PATENT DOCUMENTS

| | | | |
|---|---|---|---|
| 919697 | 1/1946 | France | 128/4 |

OTHER PUBLICATIONS

Catalog sheet entiled "Lite-Pipe Anal and Rectal Instruments", Electro Surgical Instrument Co., Rochester, N.Y.

Obliterative Suture Technique for Internal Hemorrhoidectomy, Diseases of Colon & Rectum, Sep. 1985, vol. 28, No. 9.

Catalog Sheet Surgery: General-Su, "Operating Retractor-Rectal Specula", American V. Mueller, (date unknown).

Proposal, "Weniger Anoscope", Exhibit F, Paper No. 6, Ser. No. 07/124,414.

*Primary Examiner*—Edward M. Coven
*Assistant Examiner*—Gary Jackson

[57] ABSTRACT

Hemorrhoids are removed by obliterative suturing, the patent being ambulatory and needing no anaesthetic or hospitalization. A specialized speculum for the procedure involves a probe having a flanged-cylinder anus-distending and shielding portion that is extended as a partial cylinder having a lengthwise gap between parallel edges that ideally support a hemorrhold for viewing and suturing.

4 Claims, 1 Drawing Sheet

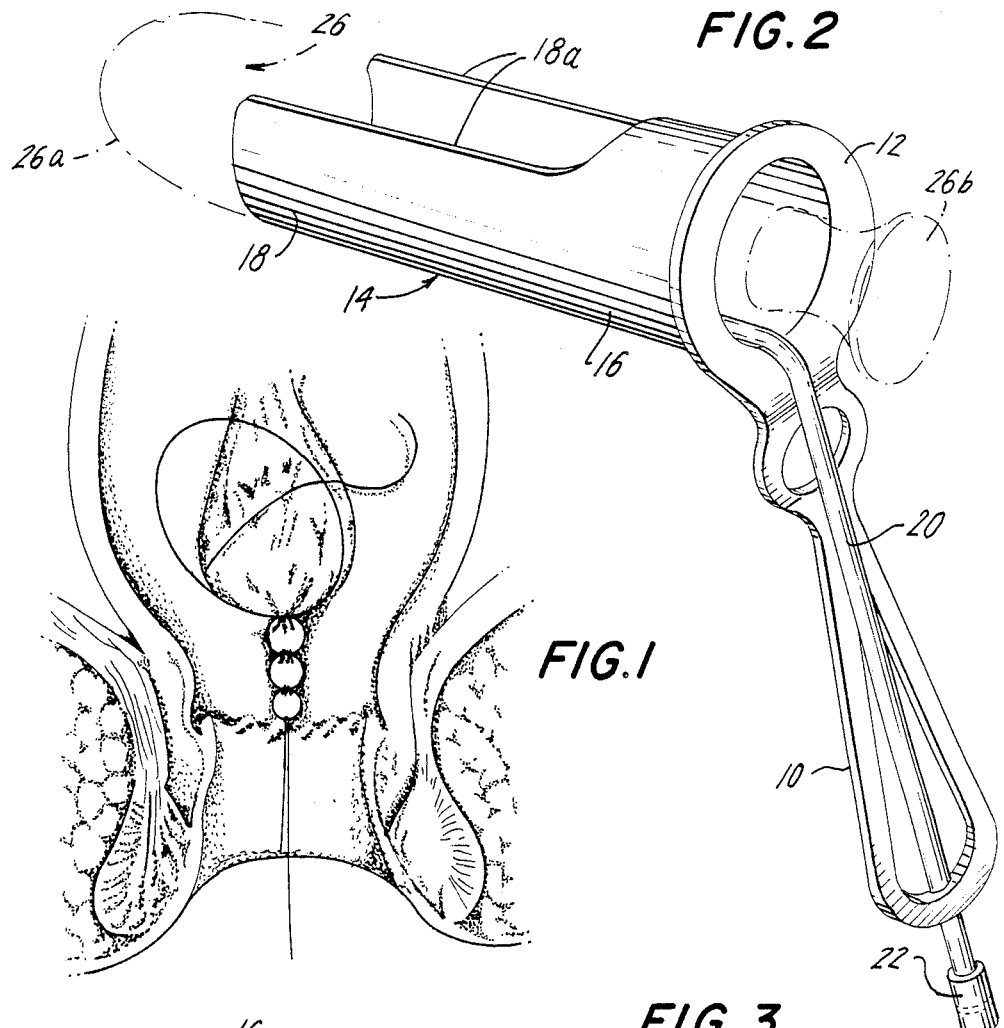
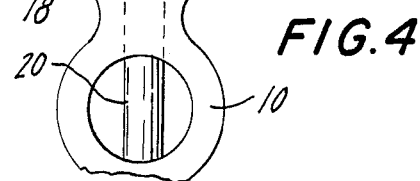
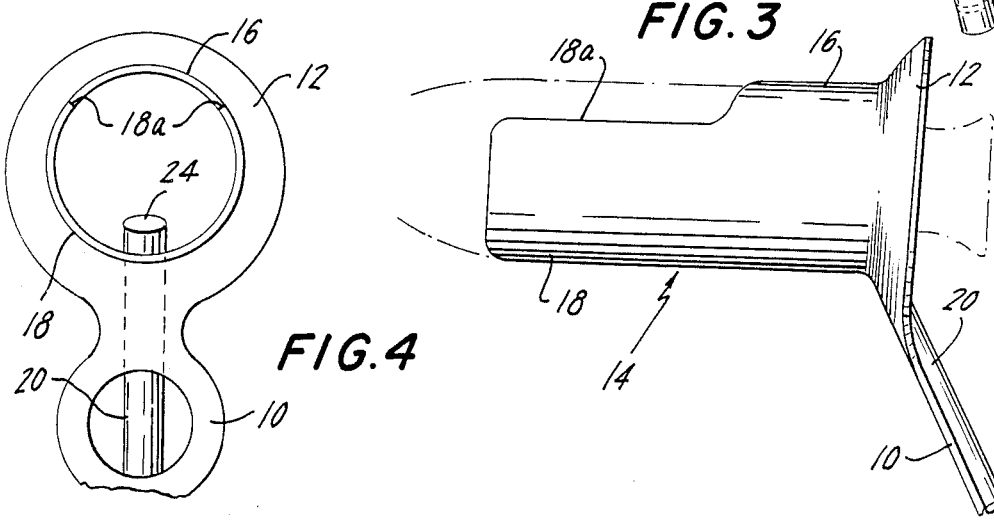

INSTRUMENT FOR INTERNAL HEMORRHOIDECTOMY

This application is a continuation of application Ser. No. 06/868,994 filed June 30, 1986 now abandoned.

The present invention relates to a novel speculum for removing hermorrhoids.

Hemorrhoidectomy as it is widely practiced commonly involves excision of the abnormal tissue and suturing of the surgically produced wounds. The patient is usually placed under general anaesthesia, which entails an inherent degree of risk. In addition, the patient invariably experiences acute pain for many days during the period of recovery, especially when defecating.

During the procedure of hemorrhoidectomy, the surgeon may encounter certain conditions that make satisfactory completion of the operation difficult or impossible. For example: (1) the patient may have a deep, funnel-shaped perianal region, surrounded by heavy gluteal musculature, an anatomic configuration which may markedly limit access to the interior of the rectum; (2) it may be impossible to draw the internal hemorrhoids out of the rectum to facilitate excision; (3) in some patients, the internal poles of the internal hermorrhoids may extend so high in the rectum as to defy efforts at total excision; (4) atypical distribution of internal hemorrhoidal tissue may leave significant symptomatic residues following the conventional surgical procedures; (5) areas of redundant rectal mucosa may be difficult and hazardous to excise; (6) unexplained excessive bleeding during surgery may induce the surgeon to seek a technique with less chance of bleeding; and (7) advanced age and/or poor general condition may preclude the use of anaesthesia.

The present invention provides an alternative to the method of removing internal hemorrhoids by excision, and it provides a novel speculum that is specialized for the novel alternative method.

Pursuant to an aspect of the invention, difficulties associated with excision of internal hemorrhoids, as enumerated above, may be managed with outstanding success by obliterative suture that has not been used heretofore in removing hemorrhoids. Committing the patient to a hospital can be avoided because the procedure can be performed without resort to general anaesthesia, by a proctologist operating without an assisting team, and in the proctologist's office. Not even local anaesthesia is needed since the rectum is generally insensitive to pain. The patient is ambulatory after the operation, and the patient is routinely spared the long period of acute pain (especially during defecation) that characterizes excision of hemorrhoids.

As a basic departure from excision, hemorrhoids are removed pursuant to one aspect of the invention by obliterative suture. The principle of the obliterative suture is the strangulation and subsequent sloughing of tissue contained within a strangulating suture, such as a continuous lock-stitch suture. At the same time, the mucosal and submucosal tissues that are included in the suture but that lie external to the strangulating effects of the suture, are viable and well-approximated. Within 10 to 14 days, the obliterated tissues have sloughed and the wound has healed.

The obliterative suture procedure of the present invention has advantages over a known "rubber-band" ligation procedure which can be used with only small hemorrhoid conditions, and which may entail follow-up treatment in case of dislodged rubber bands and which may need repeated treatments for large hemorrhoids.

A related aspect of the invention resides in providing a novel speculum to afford an unassisted proctologist with working access to the hemorrhoids for obliterative suture.

The novel speculum resembles various instruments that have been used for many years by proctologists in examining the rectum of patients. Generally, the examination instruments comprise a hollow elongated conical structure carried by a handle. A gap is formed along the conical structure remote from the handle, providing a space where the hemorrhoid can be viewed. Those instruments, while suitable for performing examination, are seriously deficient for the novel obliterative suture method.

Chelsea-Eaton specula for examination and for operation have also been known for many years. Those specula have what may be called a probe portion carried by a handle. The probe portion comprises a particylinder—an incomplete or interrupted cylinder having a uniform end-to-end gap—and a correspondingly interrupted flange at the handle end of the parti-cylinder. While the Chelsea-Eaton operating speculum is suitable for use in excising hemorrhoids, implicitly involving an anaesthetized patient, it is unsuitable for the novel obliterative suture method of hemorrhoid removal.

A practical necessity for the novel hemorrhoid removal method, the novel speculum comprises a hollow cylinder bearing a flange and a handle at one end. The cylinder includes an outer or first full-circle cylindrical portion extending from the handle, a full-circle flange at the handle end of the outer cylindrical portion, and an inner or second parti-cylindrical portion extending continuously from the outer portion, the inner portion having a uniform gap along its length. The probe is inserted into the anus and the rectum of a patient. During insertion, an obturator fills the speculum, as is customary. The full-circle flange rests against and shields the patient's anus. The full-circle portion of the cylinder dilates the anus and covers the skin of the anal canal. The inner parti-cylindrical portion enters the rectum. When the inner probe portion is positioned so that the gap is centered at a hemorrhoid, the tissue bulges into the space provided by the probe so that it is positioned ideally for suturing. The patient is not usually anaesthetized. Despite the resulting involuntary muscular constriction, the outer cylindrical portion of the probe maintains the anal canal dilated to maintain an adequate view of the rectum. Moreover, the flange and the outer probe portion of the probe act as a shield for the anus and the anal canal (highly sensitive when no anaesthesia is used) against hurtful contact during the procedure.

The novel speculum and the novel method of hemorrhoid removal are interdependent aspects of the invention. The full advantage of the method is realized for the benefit of an ambulatory patient when the method is performed by an unassisted proctologist, without resort to anaesthesia. In turn, the novel anal speculum is a practical necessity to expeditious performance of the procedure.

The nature of the invention in its various aspects, and further novel features, will be more fully appreciated from the following detailed description and the accompanying drawings.

In the drawings:

FIG. 1 represents a sagittal section of the anal canal and rectum of a patient undergoing obliterative suturing of a hemorroid, pursuant to one of the aspects of the invention;

FIG. 2 is a perspective view of an illustrative novel anal speculum, including an obturator shown in broken lines; and FIGS. 3 and 4 are a side elevation and a left-end view, respectively, of the speculum of FIG. 1, a portion of the handle being broken away, and an obturator being shown in broken lines.

Referring first to FIGS. 2-4, the illustrative anal speculum shown includes a handle 10 as of heavy sheet metal extending integrally to a shallow conical flange 12. A hollow cylindrical probe 14 extends continuously from the inner margin of flange 12. In use, the flange bears against the external portion of the anus. The probe includes an (axially) outer portion 16 extending from the inner margin of the flange. Outer or first probe portion 16 is to distend the patient's anus. An inner or second probe portion 18 extends from probe portion 16, to penetrate deeper so as to extend into the rectum.

Outer probe portion 16 is a hollow complete cylinder, extending all the way around the cylinder's axis, and flange 12 also extends all the way around the cylinder's axis. Flange 12 slopes outward and away from probe portion 16. The inner portion 18 of the probe (which projects deeper into the patient) has the shape of a cylinder of the same diameter as probe portion 16, but portion 18 extends only partway around the cylindrical axis to parallel longitudinal edges 18a. A gap is formed between edges 18a.

A metal tube 20 filled with light-transmitting fibers extends along handle 10 from a coupling 22 to a light-emitting end 24, for illuminating the tissue that is positioned in the gap of inner probe portion 18. Coupling 22 is to be joined to another fitting of a fiber-optical light source (not shown). Such illumination means is conventionally a part of examining and operating specula.

An obturator 26 is used with the novel speculum, to provide a single composite structure during insertion. The obturator slides lengthwise within probe 14; it has a bullet-nose end portion 26a that projects from inner portion 18 of the probe and it has a handle 26b that is used to remove the obturator when the speculum has been inserted. While obturators are conventional, the obturator used here is to be shaped to be complementary to this speculum. A shoulder limits the inward motion of the obturator and leaves the handle 26b in proper position as shown.

In use, the speculum and its obturator are inserted as a unit and positioned in the patient's anus and rectum. The gap between edges 18a is arranged to flank one of the patient's hemorrhoids. After insertion of the speculum, the obturator is withdrawn, allowing the unsupported hemorrhoid to bulge into the hollow of the speculum to a controlled extent. Outer probe portion 16 maintains the anus firmly distended despite a tendency of the sphincter to contract. Particularly when no anaesthetic is used, this tendency of the anus to contract is strong. In this way, probe portion 16 assures a clear view of the hemorrhoid and maintains ample access for the proctologist to perform the operation.

The obliterative suturing procedure is then carried out by the proctologist, without need for an assistant. A suitable suture such as a 00 chromic suture is used to form a lock-stitch along the hemorrhoid. As seen in FIG. 1, it is best to start just above the mucutaneous junction, where the skin of the anal canal adjoins the mucosa of the rectum. The lock-stitch suture is continued upward (or inward) as necessary. The obliterative suture may be continued beyond the upper pole of the internal hemorrhoid to include a wide strip of redundant mucosa. The suture then returns as a lock-stitch to the lower end and is tied to the original knot. The superposed row of lock-stitches is not absolutely necessary, but is useful in preventing the escape of fragments of the tissue from the strangulating effect of the first row. Traction on each suture as it is placed facilitates placement of the following suture and allows inclusion of the submucosal layer in the suture.

During this procedure, both probe portion 16 and flange 12 shield highly sensitive tissues of the fully conscious patient from the instruments used in the procedure. This is important both when no anaesthetic is used and when some local anaesthetic is used. The tissue of the rectum is virtually insensitive to pain.

The described procedure is repeated for each of the hemorrhoids to be removed. The patient is ambulatory, and can leave the proctologist's office without a hospital stay, as is customary after excision of hemorrhoids. The strangulated tissue sloughs off after 10 to 14 days, without the extreme pain that is routinely experienced by patients following excision of hemorrhoids.

The speculum of FIGS. 2-4 in an optimal example has a probe 14 that is 2½ inches long, outer probe portion 16 being 1-inch long and inner probe portion 18 being 1½ inches long. Probe 14 is uniformly cylindrical, portion 16 being a full cylinder and probe portion 18 being parti-cylindrical. Edges 18a in this example are spaced apart by an angle of somewhat more than 90° about the cylindrical axis, so that edges 18a are spaced apart along a straight line by about one inch. Flange 12 is about 3/16-inch wide.

A speculum having these dimensions is suitable for most patients. The 1-inch length of probe portion 16 is optimum because the length of the anal canal among different patients varies little, while making probe portion 16 significantly longer tends to interfere with viewing and manipulating access to the rectum. Considering the diameter of outer probe portion 16, the anal canal and rectum of most patients can usually be distended, without causing pain, to a 1⅛ inch diameter, which is practical for this procedure, but with some patients it may be necessary to limit the diameter of the probe to ⅞-inch.

The foregoing represents a detailed description of the novel method and instrument in their presently preferred form. However, because of the latitude of variations that may be made by those skilled in the art, the claims should be construed broadly in accordance with the true scope and spirit of the invention.

What is claimed is:

1. A speculum especially effective for hemorrhoidectomy of a patient by obliterative suture, including a handle, a flange, and a hollow cylindrical probe, said flange having inner and outer margins, said handle extending from the flange, said probe being joined to said flange at said inner margin and said flange sloping outward away from said probe, said probe having a uniform diameter of between ⅞ inch and 1⅛ inches and thereby avoiding such large anal distension as to require general anaesthesia for most patients while providing sufficient space for the obliterative suture procedure, said probe including a first probe portion in the form of a full cylinder extending from the inner margin of the flange, said first probe portion being approximately one inch long for distending the anus of the patient and shielding the anus during the procedure, and said probe including a second probe portion extending continuously from the first probe portion in the form of an incomplete cylinder, said second probe portion having spaced-apart edges parallel to the cylindrical axis and thus forming a gap, the second probe portion being approximately 1½ inches long and said edges subtending a minor angle from the cylindrical axis that is somewhat greater than 90° such that, when the gap is disposed in line with a hemorrhoid, the hemorrhoid bulges into the hollow space of the second probe portion while affording space for the obliterative suture procedure.

2. A speculum especially effective for hemorrhoidectomy of a patient by obliterative suture, including a handle, a flange, and a hollow cylindrical probe, said flange having inner and outer margins, said handle extending from the flange, said probe being joined to said flange at said inner margin and said flange sloping outward away from said probe, said probe having a uniform diameter of approximately 1⅛ inches and thereby avoiding such large anal distension as to require general anaesthesia for most patients while providing sufficient space for the obliterative suture procedure, said probe including a first probe portion in the form of a full cylinder extending from the inner margin of the flange, said first probe portion being approximately one inch long for distending the anus of the patient and shielding the anus during the procedure, and said probe including a second probe portion extending continuously from the first probe portion in the form of an incomplete cylinder, said second probe portion having spaced-apart edges parallel to the cylindrical axis and thus forming a gap, the second probe portion being substantially longer than one inch and said edges subtending a minor angle from the cylindrical axis that is somewhat greater than 90° such that, when the gap is disposed in line with a hemorrhoid, the hemorrhoid bulges into the hollow space of the second probe portion while affording space for the obliterative suture procedure.

3. A speculum as in claim 2, wherein said edges are about one inch apart.

4. A speculum as in claim 2, wherein said second probe portion is approximately 1½ inches long.

* * * * *